US009024067B2

(12) United States Patent
Selwood

(10) Patent No.: US 9,024,067 B2
(45) Date of Patent: May 5, 2015

(54) PROCESS FOR PREPARING CARBOXYLIC ACID AMIDES USEFUL IN THE TREATMENT OF MUSCULAR DISORDERS

(75) Inventor: David Selwood, Hertfordshire (GB)

(73) Assignee: Canbex Therapeutics Limited, London (GB)

( * ) Notice: Subject to any disclaimer, the term of this patent is extended or adjusted under 35 U.S.C. 154(b) by 911 days.

(21) Appl. No.: 13/254,409

(22) PCT Filed: Mar. 3, 2010

(86) PCT No.: PCT/GB2010/000386
§ 371 (c)(1),
(2), (4) Date: Dec. 15, 2011

(87) PCT Pub. No.: WO2010/116116
PCT Pub. Date: Oct. 14, 2010

(65) Prior Publication Data
US 2012/0101301 A1    Apr. 26, 2012

(30) Foreign Application Priority Data

Mar. 6, 2009   (GB) .................................. 0903956.1

(51) Int. Cl.
*C07C 231/14*   (2006.01)
*C07C 231/02*   (2006.01)
*C07C 231/12*   (2006.01)

(52) U.S. Cl.
CPC .............. *C07C 231/02* (2013.01); *C07C 231/12* (2013.01)

(58) Field of Classification Search
None
See application file for complete search history.

(56) References Cited

FOREIGN PATENT DOCUMENTS

WO    2005/080316 A2    9/2005

OTHER PUBLICATIONS

Gangjee et al., Synthesis of Classical, Four-Carbon Bridged 5-Substituted Furo[2,3-d]pyrimidine and 6-substituted Pyrrolo[2,3-d]pyrimidine Analogues as Antifolates. Journal of Medicinal Chemistry, 2005, 48, 5329-5336.*
Carruthers, W., Some Modern Methods of Organic Synthesis, Cambridge University Press, Cambridge, MA, Third Edition, pp. 81-90 (1990).
Greene, Theodora W. et al., Protective Groups in Organic Synthesis, John Wiley & Sons, Inc., New York, NY, Second Edition, 493 pages, (1991).
Hoffmann, Reinhard W., "Wittig and His Accomplishments: Still Relevant Beyond His 100th Birthday," Angew. Chem. Int. Ed., vol. 40*8):1411-1416 (2001).
Hoi, P.M. et al., "Vascular pharmacology of a novel cannabinoid-like compound, 3-(5-dimethylcarbamoyl-pent-1-enyl)-N-)2-hydroxy-1-methyl-ethyl)benzamide (VSN16) in the rat," British Journal of Pharmacology, vol. 152:751-764 (2007).
Hopper, Allen T. et al., "Design, Synthesis, and Biological Evaluation of Conformationally Constrained aci-Reductone Mimics of Arachidonic Acid," J. Med. Chem., vol. 41:420-427 (1998).
Hoye, Rebecca C. et al., "Synthesis of Elenic Acid, an Inhibitor of Topoisomerase II," J. Org. Chem., vol. 64:2450-2453 (1999).
Maercker, Adalbert, "The Wittig Reaction," Organic Reactions, Wiley & Sons Inc., vol. 14, chapter 3, pp. 270-490 (1965).

* cited by examiner

*Primary Examiner* — Michael Barker
*Assistant Examiner* — Po-Chih Chen
(74) *Attorney, Agent, or Firm* — Nelson Mullins Riley & Scarborough LLP; Cynthia L. Kanik

(57) ABSTRACT

The present invention relates to a process for preparing a compound of formula wherein: $R^2$ is cycloalkyl or alkyl, each of which may be optionally substituted; Y is —$CONR^3R^4$, —CN or $CO_2R^5$; $R^3$, $R^4$ and $R^5$ are each independently H or alkyl; n is 1 to 6; wherein said process comprising the steps of: (i) treating a compound of formula (IV), where $R^1$ is alkyl, with a compound of formula (V) and forming a compound of formula (IIIb); (ii) treating said compound of formula (IIIb) with a compound of formula (I1) to form a compound of formula (I).

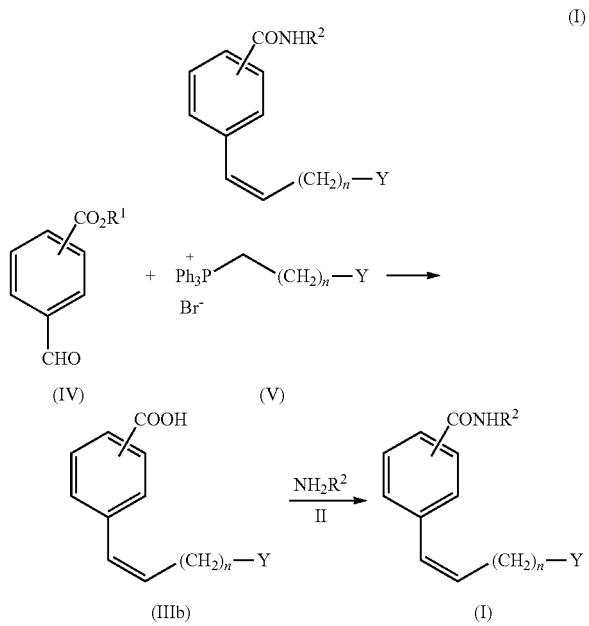

47 Claims, No Drawings

PROCESS FOR PREPARING CARBOXYLIC ACID AMIDES USEFUL IN THE TREATMENT OF MUSCULAR DISORDERS

RELATED APPLICATIONS

This application is a 35 U.S.C. §371 national stage filing of PCT Application No. PCT/GB2010/000386 filed on Mar. 3, 2010, which claims priority to, and the benefit of, Great Britain Patent Application No. 0903956 filed Mar. 6, 2009. The contents of the aforementioned applications are hereby incorporated by reference.

The present invention relates to a process for preparing compounds therapeutically useful in the treatment of muscular disorders, gastrointestinal disorders, or for controlling spasticity or tremors.

BACKGROUND TO THE INVENTION

WO2005/080316 (in the name of University College London) discloses compounds capable of modulating cannabinoid or cannabinoid-like receptors, including VSN-16, the structure of which is shown below.

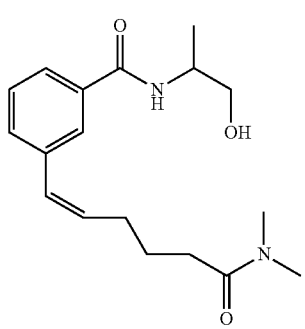

VSN-16

Initial studies demonstrated that VSN-16 and related compounds exhibited a marked effect on spasticity in CREAE mice, providing strong evidence that a selective inhibition of spasticity was achieved without producing significant adverse CNS effects. Studies also demonstrated that the compounds inhibited gastrointestinal motility, as measured using a colonic propulsion test. More recent pharmacological studies have established that VSN-16 and related compounds appear to act on a putative novel cannabinoid receptor of the vasculature (P. M. Hoi, C. Visintin, M. Okuyama, S. M. Gardiner, T. Bennett, D. Baker, D. L. Selwood and C. R. Hiley; *British Journal of Pharmacology*, 2007, 1-14). VSN-16 is understood to act on the endothelium to release nitric oxide and activate $K_{Ca}$ and $TRPV_1$. Its solubility is believed to play a significant role in bringing about peripheral cannabinoid-like effects without accompanying central or severe cardiovascular responses.

WO2005/080316 discloses the preparation of VSN-16 as shown in Scheme 1 below.

Scheme 1

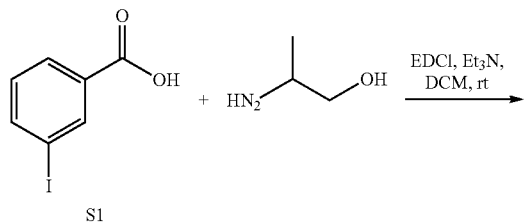

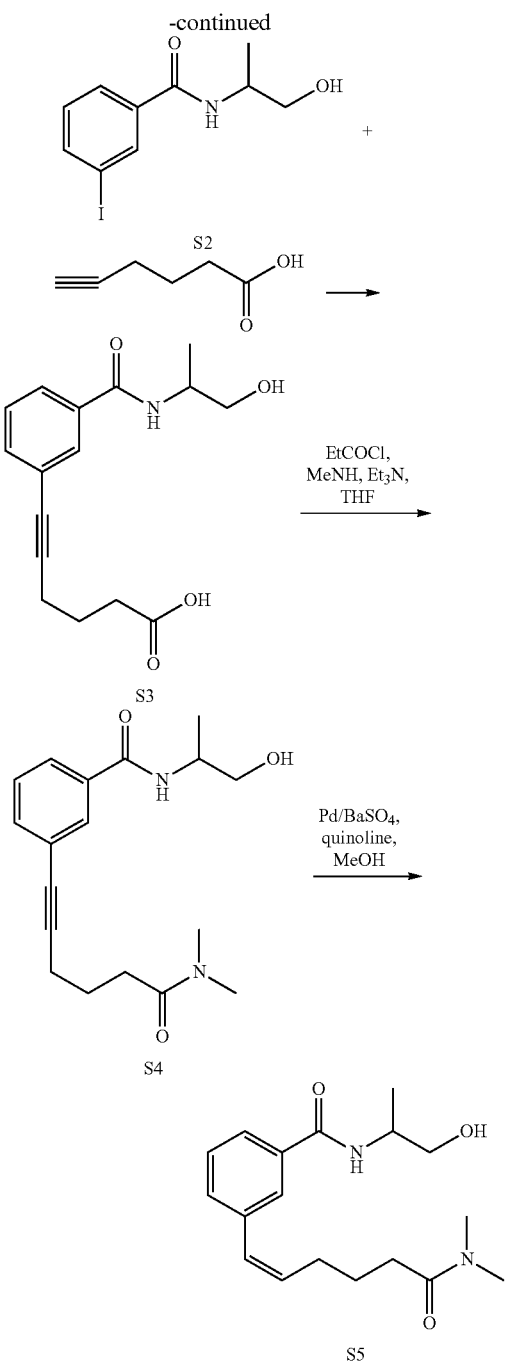

In brief, a palladium catalysed Songashira coupling reaction was used to insert a variety of alkyl side chains into 3-iodo methyl benzoate. The target compounds (S5) and related analogues were synthesised by a simple four-step route. First, the acid (S1) was reacted with DL alaminol in the presence of a diimide (EDCI) to give the amide (S2) in good yield. Palladium-catalysed coupling [Hoye, R. C. et al, *J. Org. Chem.* 1999, 64, 2450-2453; Hopper, A. T. et al, *J. Med. Chem.* 1998, 41, 420-427] of the amide with the alkyne acid in the presence of $Cu^{I}I$ and pyrrolidine proceeded smoothly to give the alkyne (S3). The acid (S3) was quantitatively transformed into (S4) using ethylchloroformate and dimethylamine HCl. Lindlar catalysed reduction yielded the target alkene (S5). Alternatively, (S4) can be reduced with borohydride (polymer supported), $(CH_3COO)_2Ni.4H_2O$, MeOH, and $H_2$ at atmospheric pressure (P. M. Hoi, C. Visintin, M.

Okuyama, S. M. Gardiner, T. Bennett, D. Baker, D. L. Selwood and C. R. Hiley; *British Journal of Pharmacology*, 2007, 1-14). The flexibility of this method allows the synthesis of a large number of different compounds using a range of alkynes for the Sonogashira coupling, or by starting with a different amine for the amide formation in the first step. However, the main drawback of this synthetic route is that the Lindlar catalytic reduction of intermediate (S4) yields a mixture of E- and Z-isomers of the resulting alkenyl compounds, requiring separation by reverse phase HPLC. This technique is both costly and time consuming, thereby rendering the method unsuitable for large scale synthesis.

The present invention seeks to provide an alternative process for preparing VSN-16 and related compounds. More specifically—although not exclusively—the invention seeks to provide an improved process to those previously described in the art, and/or a process that is suitable for scale-up.

STATEMENT OF INVENTION

A first aspect of the invention relates to a process for preparing a compound of formula I,

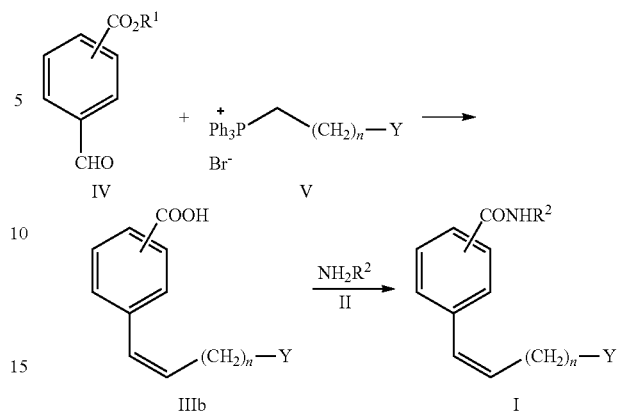

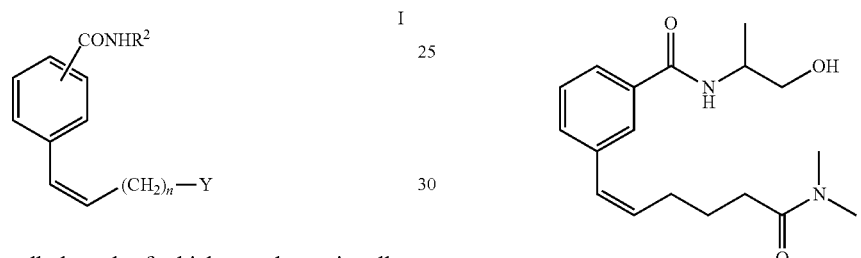

wherein:
$R^2$ is cycloalkyl or alkyl, each of which may be optionally substituted;
Y is $-CONR^3R^4$, $-CN$ or $CO_2R^5$;
$R^3$, $R^4$ and $R^5$ are each independently H or alkyl;
n is 1 to 6;
said process comprising the steps of:
(i) treating a compound of formula IV, where $R^1$ is alkyl, with a compound of formula V to form a compound of formula IIIb;
(ii) treating said compound of formula IIIb with a compound of formula II to form a compound of formula I;

A second aspect of the invention relates to a process for preparing VSN-16 said process comprising the steps of:
treating a compound of formula IV.1 with a compound of formula V.1 to form a compound of formula IIIb.1;
treating said compound of formula IIIb.1 with a compound of formula IIb.1, where PG is a protecting group, to form a compound of formula Ib.1; and
removing protecting group PG from said compound of formula Ib.1 to form VSN-16

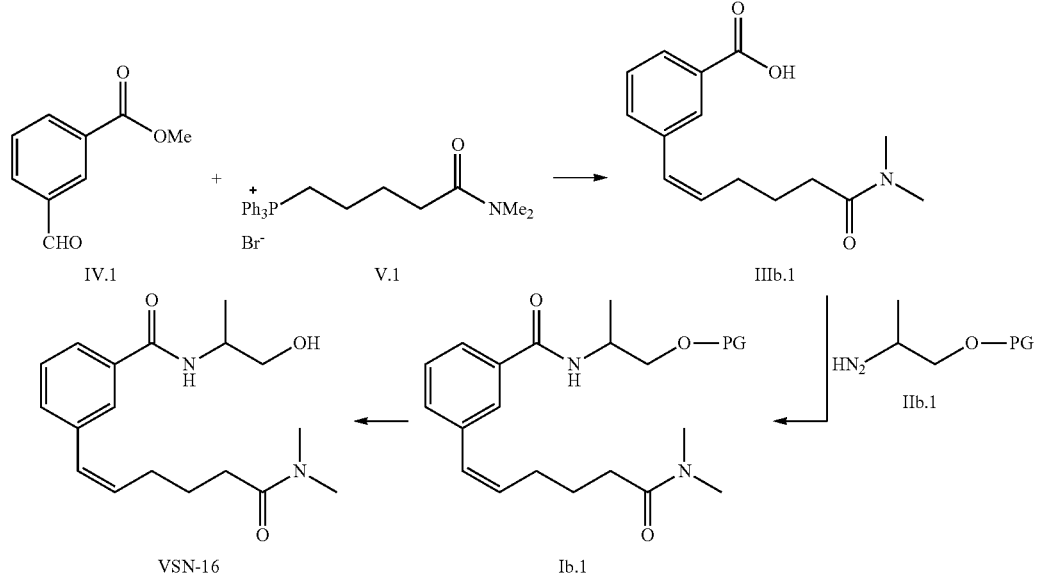

DETAILED DESCRIPTION

The present invention relates to a process for preparing compounds of formula I, as defined herein.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-10}$ alkyl group, more preferably still, a $C_{1-6}$ alkyl group. Particularly preferred alkyl groups include, for example, methyl, ethyl, propyl, isopropyl, butyl, isobutyl, tert-butyl, pentyl and hexyl. Suitable substituents include, for example, alkyl, hydroxy, halo-, alkoxy-, nitro-, COOH, $CO_2$-alkyl, alkenyl, CN, $NH_2$, $CF_3$ or a cyclic group.

As used herein, the term "cycloalkyl" refers to a cyclic alkyl group which may be substituted (mono- or poly-) or unsubstituted. Preferably, the cycloalkyl group is a $C_{3-12}$ cycloalkyl group, more preferably a $C_{3-6}$ cycloalkyl group. Suitable substituents include, for example, alkyl, hydroxy, halo-, alkoxy-, nitro-, COOH, $CO_2$-alkyl, alkenyl, CN, $NH_2$, $CF_3$ or a cyclic group.

In one preferred embodiment, the invention relates to a process for preparing a compound of Ia

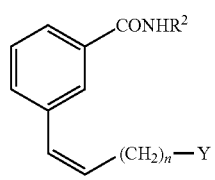

Ia wherein $R^2$, n and Y are as defined in claim 1.

In one preferred embodiment, n is 2, 3 or 4. Even more preferably, n is 3.

In one preferred embodiment, Y is —$CONR^3R^4$ or —CN. More preferably, Y is —$CONR^3R^4$.

In one preferred embodiment, $R^3$ and $R^4$ are each independently H or methyl.

In one particularly preferred embodiment, Y is —$CONMe_2$ or CN. Even more preferably, Y is —$CONMe_2$.

In one preferred embodiment, $R^2$ is alkyl or cycloalkyl, each of which may be optionally substituted with OH or a halogen.

Where $R^2$ is cycloalkyl, preferably the cycloalkyl is a $C_3$-cycloalkyl, i.e. a cyclopropyl group.

In one preferred embodiment, $R^2$ is alkyl optionally substituted with OH or halogen. Preferably, the alkyl is branched.

Even more preferably, $R^2$ is alkyl optionally substituted with OH.

In an even more preferred embodiment, $R^2$ is

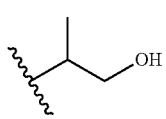 [SMILES: *C(C)CO]

In one preferred embodiment, the invention relates to a process for preparing a compound selected from the following:

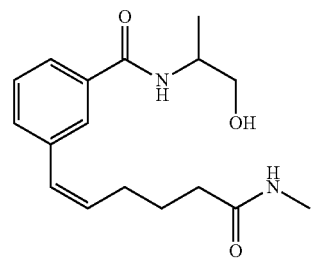

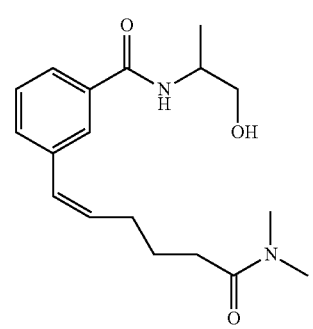

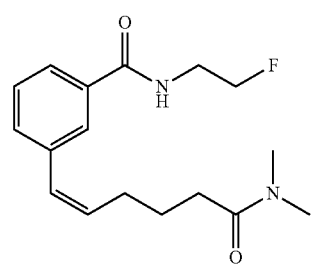

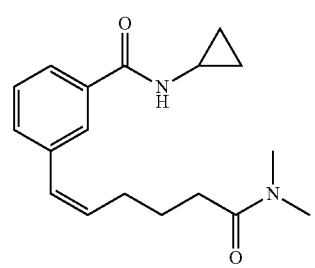

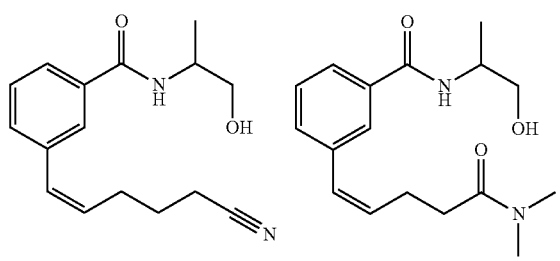

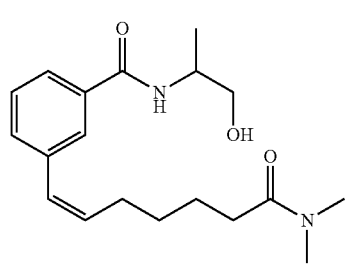

-continued

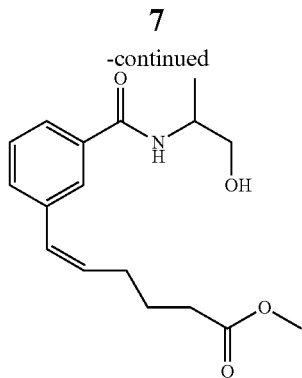

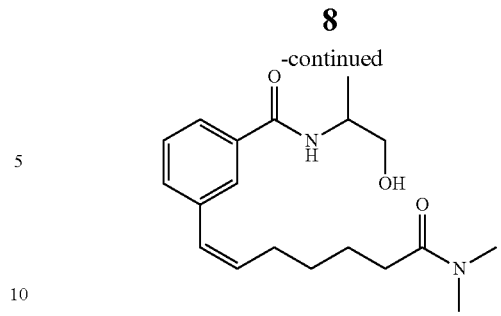

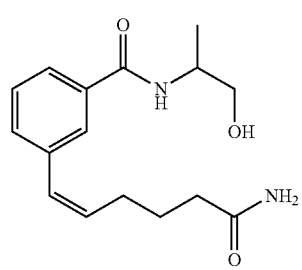

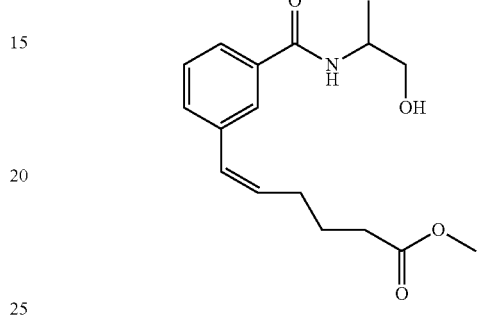

More preferably, the invention relates to a process for preparing a compound selected from the following:

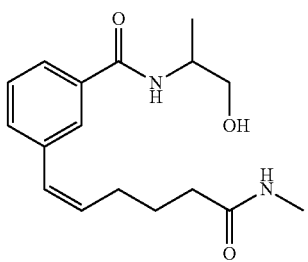

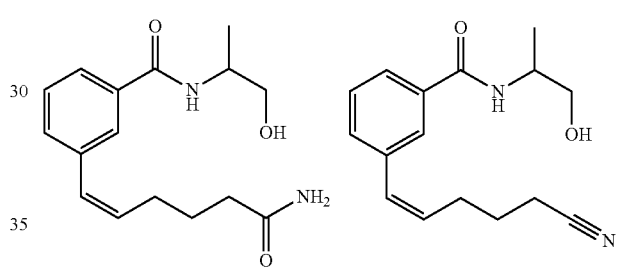

In one highly preferred embodiment, the invention relates to a process for preparing VSN-16:

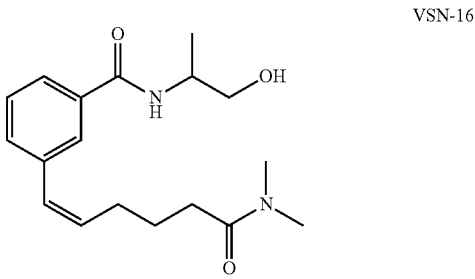 [SMILES: CC(CO)NC(=O)c1cccc(/C=C\CCCC(=O)N(C)C)c1]

VSN-16

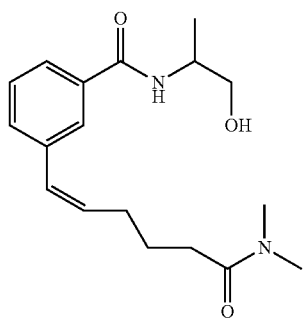

Step (i)—Wittig Reaction

Step (i) of the process involves a Wittig reaction (Maercker, A. *Org. React.* 1965, 14, 270-490 (Review); W. Carruthers, *Some Modern Methods of Organic Synthesis*, Cambridge University Press, Cambridge, UK, 1971, pp 81-90; (ISBN 0-521-31117-9); R. W. Hoffmann (2001), *Angewandte Chemie International Edition* 40 (8): 1411-1416) between an aromatic aldehyde of formula IV and a triphenylphosphonium compound of formula V.

Preferably, the Wittig reaction is carried out using a compound of formula V containing an amide group or a free acid group.

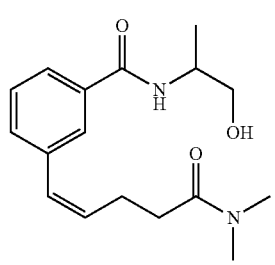

Thus, in one preferred embodiment, the compound of formula V used in step (i) is an amide compound of formula Va

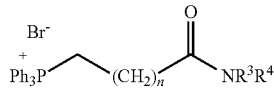

wherein $R^3$ and $R^4$ are both alkyl, more preferably methyl.

In one preferred embodiment of the process, the compound of formula V used in step (i) is dissolved in dichloromethane. Preferably, the dichloromethane is anhydrous.

In one preferred embodiment, step (i) comprises treating the compound of formula V with potassium hexamethyldisilazide in THF or toluene prior to addition of the compound of formula IV.

Preferably, the potassium hexamethyldisilazide is added at a temperature of less than about 5° C. More preferably, the temperature is about 0° C.

In one preferred embodiment, the compound of formula IV is dissolved in THF.

Preferably, the compound of formula IV is added to the reaction mixture at a temperature of less than about 5° C., more preferably less than about 4° C., even more preferably, less than about 3° C.

The compound of formula Va may itself be prepared from a compound of formula Vb. Thus, in one preferred embodiment, the process of the invention further comprises the step of preparing a compound of formula Va from a compound of formula Vb.

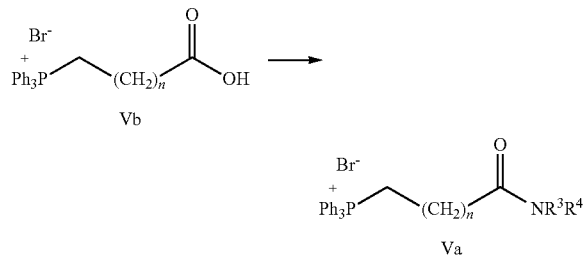

Preferably, the process comprises treating said compound of formula Vb with (a) ethyl chloroformate and triethylamine to form a mixed anhydride; and (b) reacting the mixed anhydride with an amine salt $NHR^3R^4 \cdot HCl$.

More preferably, the amine salt $NHR^3R^4 \cdot HCl$ is dimethylamine.HCl.

Preferably, step (a) is carried out in THF or anhydrous dichloromethane.

Preferably, the amine salt $NHR^3R^4 \cdot HCl$ used in step (b) (e.g. dimethylamine.HCl) is recrystallised from methanol/diethyl ether prior to use.

Preferably, the compound of formula Va is purified by trituration with diethyl ether.

As mentioned above, the Wittig reaction can also be carried out using a compound of formula V containing a free acid group. Thus, in an alternative preferred embodiment of the invention, the compound of formula V used in step (i) is of formula Vb

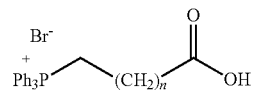

Preferably, for this embodiment, step (i) comprises adding sodium hydride in a mixture of anhydrous dichloromethane and anhydrous THF to a mixture of said compound of formula Vb in anhydrous dichloromethane.

In one preferred embodiment, step (i) comprises hydrolysing the crude product formed from the reaction of VI with V. Preferably, the crude product is hydrolysed with aqueous sodium hydroxide in methanol.

Separation of Isomers IIIa and IIIb

The Wittig reaction of step (i) yields a mixture of isomers IIIa and IIIb, corresponding to the E- and Z-isomers respectively.

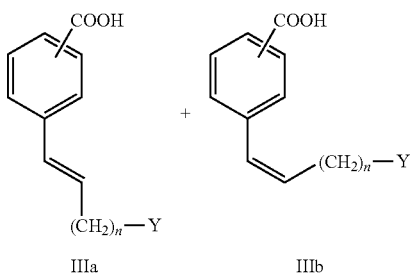

Isomer IIIa is preferably removed and isomer IIIb taken through to the final product.

Preferably, the process of the invention comprises the step of separating isomer IIIb from the mixture of isomers IIIa and IIIb prior to the commencement of step (ii)

In one particularly preferred embodiment of the invention, isomers IIIa and IIIb are separated by forming their respective salts. Advantageously, the salts of isomers IIIa and IIIb can be readily separated in view of their differing solubilities.

Thus, one highly preferred embodiment of the invention comprises the steps of:
(a) forming a salt of isomers IIIa and IIIb;
(b) separating the salt of isomer IIIb from the salt of isomer IIIa; and
(c) treating the salt of isomer IIIb obtained in step (b) to form isomer IIIb.

Preferably, the salt forms of isomers IIIa and IIIb can be separated by crystallisation, i.e. step (b) comprises separating the salt of isomer IIIb from the mixture by crystallisation. Advantageously, this avoids the need for costly and time consuming purification using reverse phase HPLC, as required by processes for preparing VSN-16 and analogues thereof known in the art to date. Moreover, the ability to separate the E- and Z-isomers IIIa and IIIb by crystallisation renders the process suitable for scale-up and contributes to an improved overall yield.

Any suitable salt can be used, providing that the salt form of isomers IIIa and IIIb can be readily separated by routine techniques. Suitable salts will be familiar to the skilled person.

In one preferred embodiment, the process involves forming the 4-dimethylaminopyridine (DMAP) salt. Thus, step (a) comprises treating the mixture of isomers IIIa and IIIb with 4-dimethylaminopyridine (DMAP) to form the corresponding DMAP salts.

Preferably, the DMAP is dissolved in ethyl acetate.

In one particularly preferred embodiment, step (b) comprises crystallising the salt form of isomer IIIb from a solvent mixture of diethyl ether and ethyl acetate. More preferably, the solvent mixture is a mixture of 1:100 to 100:1 or 1:50 to 50:1, more preferably 1:20 to 20:1, even more preferably 1:10 to 10:1 diethyl ether:ethyl acetate. Even more preferably, the solvent mixture is 9:1 diethyl ether:ethyl acetate.

In one preferred embodiment, step (c) comprises treating the salt of isomer IIIb with an acid to form isomer IIIb (in the free acid form). Preferably, the acid is HCl.

Step (ii)

Step (ii) of the process comprises reacting the compound of formula IIIb with a compound of formula II to form a compound of formula I.

In one preferred embodiment, step (ii) comprises reacting said compound of formula IIIb with a compound of formula II in the presence of a coupling agent. Suitable coupling agents will be familiar to the skilled person.

In one particularly preferred embodiment, the coupling agent is 1,1'-carbonyldiimidazole (CDI).

Preferably, for this embodiment, step (ii) comprises dissolving said compound of formula IIIb and CDI in anhydrous DMF and adding thereto said compound of formula II in anhydrous DMF.

In another particularly preferred embodiment, the coupling agent is 1-(3-dimethylaminopropyl)-ethylcarbodiimide hydrochloride (EDCI).

Preferably, for this embodiment, step (ii) comprises dissolving said compound of formula IIIb and ECDI in anhydrous dichloromethane and adding thereto N-ethyl diisopropylamine and said compound of formula II.

In one highly preferred embodiment of the invention, step (ii) comprises treating said compound of formula IIIb with a compound of formula IIb to form a compound of formula Ib

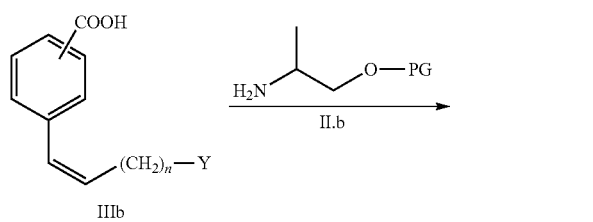

where PG is a hydroxyl protecting group. Suitable hydroxyl protecting groups will be familiar to the skilled person in the art (see for example, "Protective Groups in Organic Chemistry", Theodore W. Greene; John Wiley & Sons, Inc., New York, 1991, ISBN 0-471-62301-6).

Preferably, the hydroxyl protecting group is a silyl protecting group.

More preferably, the hydroxyl protecting group is selected from triisopropyl and trimethylsilyl.

Thus, in one preferred embodiment, the process comprises treating 2-amino-1-propanol with chorotrimethylsilane and imidazole in dichloromethane to form a trimethylsilyl-protected compound of formula IIb,

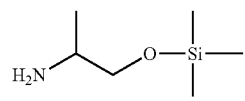

Preferably, the trimethylsilyl-protected compound of formula IIb is used directly in step (ii) in solution form without further purification.

In another preferred embodiment, the process comprises treating 2-amino-1-propanol in anhydrous dichloromethane with 2,6-lutidine and triisopropylsilyl trifluoromethane sulfonate to form a triisopropylsilyl-protected compound of formula IIb,

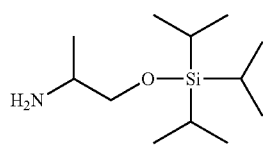

Preferably, the triisopropylsilyl-protected compound of formula IIb is used directly in step (ii) without further purification.

In one highly preferred embodiment of the invention, the compound of formula IIb is of the formula

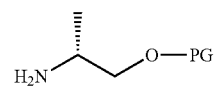

Preferably, the process of the invention further comprises the step of removing the protecting group PG from said compound of formula Ib to form a compound of formula Ia

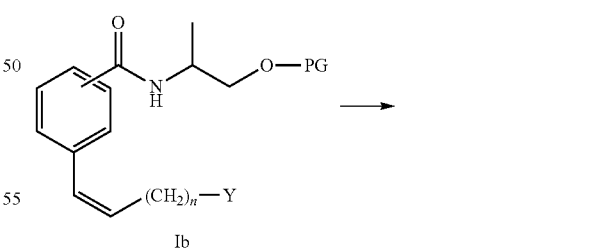

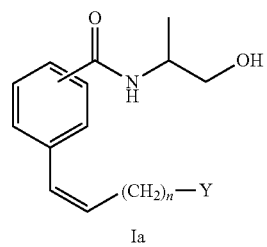

Suitable deprotecting agents and conditions will be familiar to the skilled person (see for example, "Protective Groups in Organic Chemistry", Theodore W. Greene; John Wiley & Sons, Inc., New York, 1991, ISBN 0-471-62301-6).

In one preferred embodiment, the protecting group PG is removed by treating with TBAF. Preferably, the solvent is THF.

Synthesis of VSN-16

A second aspect of the invention relates to a process for preparing VSN-16

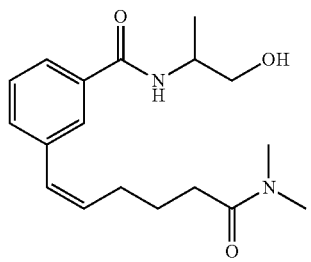

said process comprising the steps of:
treating a compound of formula IV.1 with a compound of formula V.1 to form a compound of formula IIIb.1;
treating said compound of formula IIIb.1 with a compound of formula IIb.1, where PG is a protecting group, to form a compound of formula Ib.1; and
removing protecting group PG from said compound of formula Ib.1 to form VSN-16

Preferably, protecting group PG, and the reaction conditions, solvent, temperature and the like, are as described above for the first aspect of the invention.

Step (i) of the process yields a mixture of isomers IIIa.1 and IIIb.1, which may be separated by the methodology described for the first aspect of the invention, e.g. by converting to salt form and separating by crystallisation.

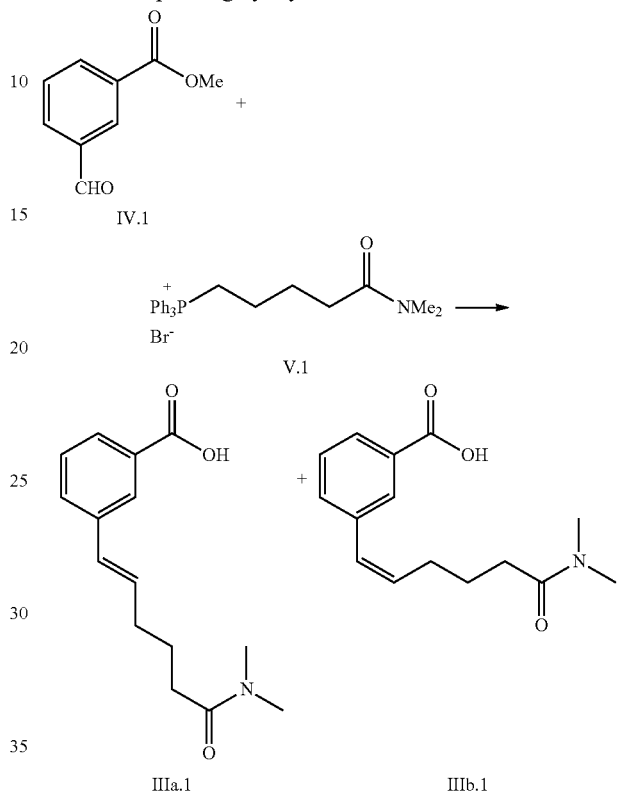

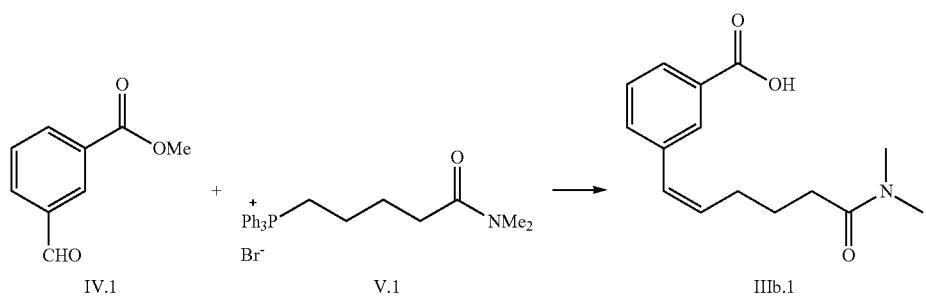

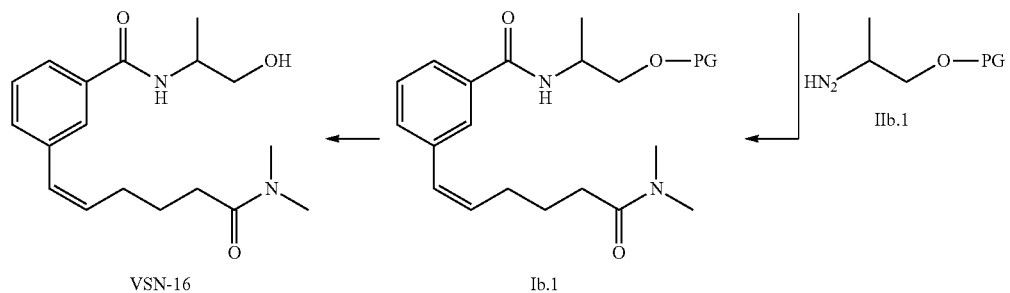

The present invention is further described by non-limiting example.

EXAMPLES

One preferred embodiment of the claimed process is set forth in Scheme 2, further details of which are described in the following examples.

Scheme 2:

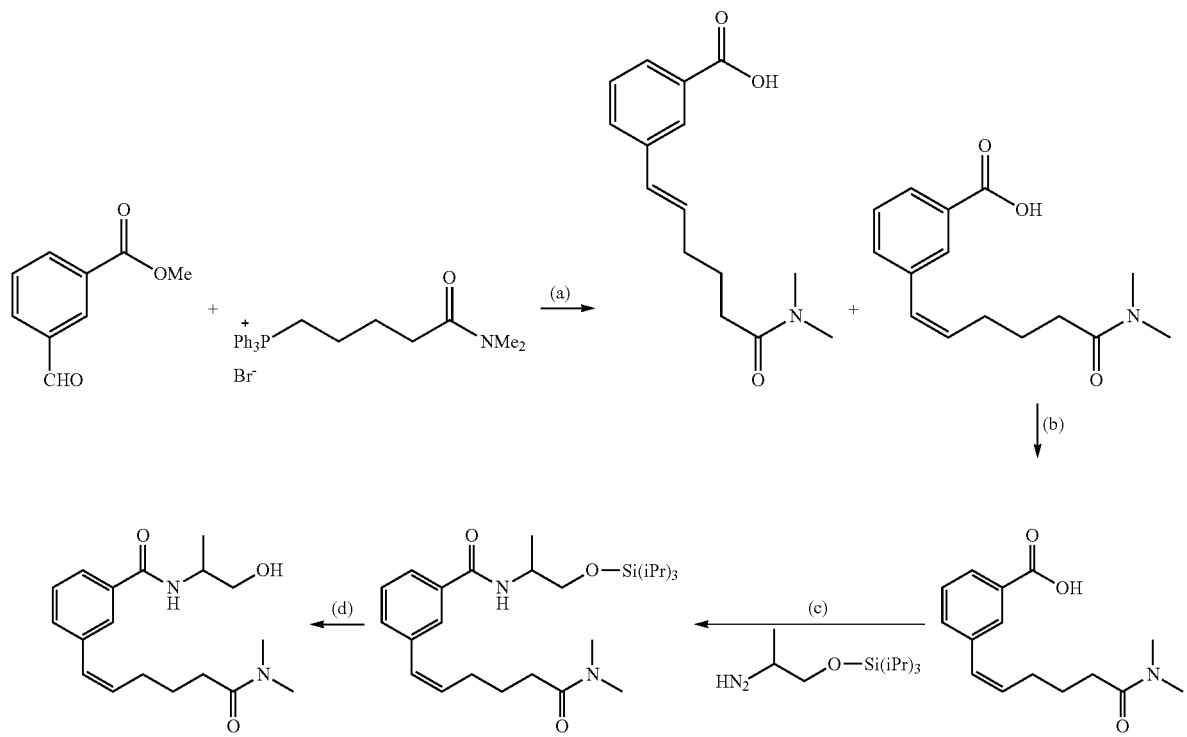

(a) (i) anhydrous CH$_2$Cl$_2$, potassium hexamethyl disilazide, THF under N$_2$ atmosphere, < 10° C.; (ii) NaOH, MeOH; (b) (i) DMAP (EtOAc, Et$_2$O); (ii) separation of isomers; (iii) HCl; (c) (i) EDCl, CH$_2$Cl$_2$, N-ethyl diisopropylamine or (ii) CDl, DMF N-ethyl diisopropylamine; (d) TBAF/THF.

N,N-dimethylamino 4-(carboxybutyl)triphenylphosphonium bromide 4-(carboxybutyl)triphenylphosphonium bromide (140 g, 0.315 mol, 1 equiv) was charged in a reactor and dichloromethane (650 ml, 4.5 vols) was added. Triethylamine (dried on molecular sieves; 95 ml, 2.1 equiv) was charged and the reaction mixture was cooled down to −10° C. Ethyl chloroformate (40 ml, 1.05 equiv) was added dropwise and the mixture was stirred for another 15 min at −10° C.

A solution containing dimethylamine hydrochloride (freshly crystallised from methanol/ether; 78 g, 3 equiv) and triethylamine (200 ml, 4.5 equiv) in dichloromethane (1000 ml, 7 vols) was prepared.

This solution was stirred for 40 min at room temperature and added dropwise to the reaction mixture at −10° C. The temperature was kept between −10 and −15° C. during all the addition. The reaction was left to warm up to room temperature. The reaction was stirred at room temperature overnight. The mixture was treated with 2 l of saturated NaHCO$_3$ solution. The aqueous phase was extracted with dichloromethane (1×2 l and 2×1 l). Organics were combined and dried over MgSO$_4$ and filtered. The volatiles were removed under vacuum. The residue was triturated with 350 ml of diethyl ether. The solid was filtered and triturated with hot diethyl ether for 5 hours. The suspension was cooled down and the solid filtered. The solid was dried under vacuum to give 130.9 g of a white solid (90% yield).

$^1$H NMR (CDCl$_3$) 7.65-8.0 (m, 15H); 3.7 (m, 2H); 3.0 (s, 3H); 2.8 (s, 3H), 2.5 (t, J=7 Hz, 2H); 1.9 (m, 2H), 1.7 (m, 2H).

3-[(1Z)-6-(dimethylamino)-6-oxohex-1-en-1-yl]benzoic acid

N,N-dimethylamino 4-carboxybutyltriphenylphosphonium (61.9 g, 0.13 mol, 3 equivalents) were dissolved in dry dichloromethane (150 ml, 2.4 vols) under nitrogen. The solution was cooled down to 0° C. and potassium hexamethyldisilazide (0.9M in THF; 45 ml, 5 equiv) was added dropwise at 0° C. The reaction mixture was stirred at 0° C. for another 45 min. A solution of methyl 3-formylbenzoate (7.16 g, 1 equiv) in dry THF (36 ml, 5 vols) was added keeping the temperature<4° C. The mixture was allowed to warm up to room temperature and was stirred for 18 hrs. The reaction was quenched with 2M HCl (400 ml) and extracted with dichloromethane (2×400 ml and 2×200 ml). Organics were combined, dried over MgSO$_4$, filtered and evaporated to dryness. The residue was dissolved in a mixture of sodium hydroxide 1M/methanol 4:1 (440 ml) and stirred for 18 hrs. Water (100 ml) was added to the mixture and methanol was evaporated under vacuum. Aqueous was extracted with ethyl acetate (400 ml). The pH was adjusted to pH 1 and the mixture was extracted with dichloromethane (2×400 ml and 2×200 ml). Organics were dried over MgSO$_4$, filtered and evaporated to dryness. M=22.0 g. The crude was purified by flash chromatography using dichloromethane to dichloromethane/ MeOH=95/54 as eluent. M=10.6 g 93% yield.

Isomer Separation

Acid (10.93 g, 0.042 mol) was dissolved in ethyl acetate (20 ml) and 4-dimethylaminopyridine (6.13 g, 1.2 equiv) was dissolved in warm ethyl acetate (20 ml). The DMAP solution was added to the free acid solution. The mixture was stirred at reflux temperature for 10 min. Then, the solution was allowed to cool down to room temperature slowly. A brown salt was formed, which was removed by filtration.

A mixture of diethyl ether/ethyl acetate: 9:1 (40 ml) was added and the solution was heated to reflux. The mixture was stirred and allowed to cool down overnight. A pale yellow solid was filtered and dried in-vacuo. This solid was treated with HCl (1M) and extracted with dichloromethane (3×50 ml). Organics were dried over MgSO$_4$, filtered and evaporated to dryness to give a brown oil which solidified upon standing. M=3.88 g (35.5% yield).

$^1$H NMR (CDCl$_3$) 9.7 (bs, 1H); 8.0 (m, 2H); 7.5 (m, 2H); 6.5 (d, J=11 Hz, 1H); 5.75 (m, 1H); 3.0 (s, 6H); 2.4 (m, 4H); 1.9 (m, 2H)

(R)-2-amino-1-triisopropylsilyloxypropanol (R)-2-amino-1-propanol (1.0 g, 0.0133 mol) was dissolved in dry dichloromethane (5 ml, 5 vols) and 2,6-lutidine (1.75 ml, 0.0146 mol, 1.1 equiv) was added then trisiopropylsilyl trifluoromethane sulfonate (4 ml, 0.0146 mol, 1.1 equiv) at room temperature. The temperature was controlled with a water bath. The reaction was stirred overnight at room temperature. TLC showed formation of a second spot and no trace of starting material. The mixture was washed with 15% aqueous acetic acid (3 ml). Organics were separated, dried over MgSO$_4$, filtered and evaporated to dryness to provide a brown thick oil. Petrol ether was added and a white solid formed. The solid was filtered off and the filtrate was evaporated to provide the product with a quantitative yield. The product was used without further purification.

$^1$H NMR (CDCl$_3$) 6.5 (bs, 2H); 3.8 (m, 1H); 3.6 (m, 1H); 3.4 (m, 1H); 1.4 (d, J=7 Hz, 3H)$_m$, 1.0 (m, 21H).

3-[(1Z)-6-(dimethylamino)-6-oxohex-1-en-1-yl]-N-(2-triisopropylsilyloxy-1-methyl-ethyl)benzamide The 3-[(1Z)-6-(dimethylamino)-6-oxohex-1-en-1-yl]benzoic acid previously prepared (2.19 g, 0.0083 mol, 1 equiv) and 1,1-carbonyldiimazole (1.87 g, 0.0115 mol, 1.4 equiv) were dissolved in dry dimethylformamide (15 ml, 7 vols) at 0° C. (R)-2-amino-1-triisopropylsilyloxypropanol was dissolved in a small portion of dry DMF and added.

The reaction mixture was stirred for 18 h at 50° C. DMF was removed under vacuum and the residue was co-evaporated with toluene to remove traces of DMF. The crude was dissolved in ethyl acetate (100 ml) and washed with 2M HCl (50 ml), saturated sodium bicarbonate (60 ml), water (2×50 ml) and brine (50 ml). Organics were dried over MgSO$_4$, filtered and solvent was evaporated under vacuum. The residue was purified by chromatography on silica using ethyl acetate/petrol: 2:8 to 9:1 as eluent. This provided the expected product as a white solid with 73.6% yield.

$^1$H NMR (CDCl$_3$) 7.6 (s, 1H); 7.5 (m, 1H); 7.3 (d, m, 2H); 6.6 (d, J=, 1H, 6.4 (d, J=1H); 5.65 (m, 1H); 4.2 (m, 1H); 3.7 (m, 2H); 2.9 s, 3H); 2.85 (s, 3H); 2.35 (m, 2H); 2.25 (t, J=14 Hz, 2H); 1.75 (m, 2H); 1.25 (d, J=7 Hz, 3H), 1.0 (m, 21H)

R)-3-(5-Dimethylcarbamoyl-pent-1-enyl)-N-(2-hydroxy-1-methyl-ethyl)benzamide (VSN16R 3-[(1Z)-6-(dimethylamino)-6-oxohex-1-en-1-yl]-N-(2-triisopropylsilylether-1-methyl-ethyl)benzamide (2.87 g, 0.0061 mol) was dissolved in THF (18 ml, 6 vols) and tetra n-butylammonium fluoride 1M in THF (18 ml, 3 equiv, 0.018 mol) was added at room temperature. The reaction mixture was stirred at room temperature for 18 h. The solvent was evaporated and ethyl acetate (50 ml) was added. The mixture was washed with HCL 2M (50 ml) and brine (50 ml). Organics were dried over MgSO$_4$, filtered and evaporated to dryness. The residue was purified by chromatography on silica using dichloromethane then dichloromethane/MeOH: 95/5 to provide only 438 mg of product (27.9%) as a thick yellow oil. TLC showed that some product remained in the aqueous layer. The aqueous was further extracted with ethyl acetate until no product was left in the aqueous. The crude was purified as previously to provide a thick yellow oil. The product sticks to ethyl acetate and was dissolved in dichloromethane and evaporated to dryness. M=1.3 g (70.3% yield).

$^1$H NMR (CDCl$_3$) 7.7 (m, 2H); 7.35 (m, 1H); 7.2 (m, 1H); 6.4 (d, J=12 Hz, 1H); 5.65 (m, 1H), 4.2 (m, 1H); 3.75 (dd, J=3 Hz, J=8 Hz, 1H); 3.55 (dd, J=5 Hz, J=11 Hz, 1H); 2.9 (s, 3H); 2.85 (s, 3H); 2.3 (t, J=7 Hz, 2H); 2.25 (m, 2H); 1.8 (m, 2H); 1.25 (d, J=7 Hz, 3H)

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

The invention claimed is:

1. A process for preparing a compound of formula I,

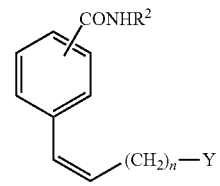

wherein:
R$^2$ is cycloalkyl or alkyl, each of which may be optionally substituted;
Y is —CONR$^3$R$^4$, —CN or CO$_2$R$^5$;
R$^3$, R$^4$ and R$^5$ are each independently H or alkyl;
n is 1 to 6;
said process comprising the steps of:
(i) treating a compound of formula IV, where R$^1$ is alkyl, with a compound of formula V to form a compound of formula IIIb;
(ii) treating said compound of formula IIIb with a compound of formula II to form a compound of formula I;

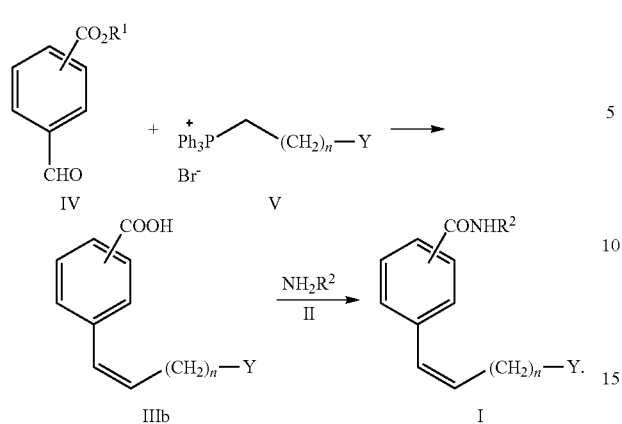

2. A process according to claim 1 wherein said compound of formula I is of formula Ia

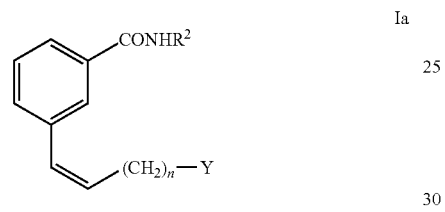

wherein $R^2$, n and Y are as defined in claim 1.

3. A process according to claim 1, wherein n is 2, 3 or 4.

4. A process according to claim 1, wherein Y is —$CONR^3R^4$ or —CN.

5. A process according to claim 4, wherein Y is —$CONMe_2$.

6. A process according to claim 1, wherein $R^2$ is alkyl optionally substituted with OH.

7. A process according to claim 6, wherein $R^2$ is

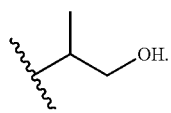 [SMILES: *C(C)CO]

8. A process according to claim 2, wherein said compound of formula I is selected from the following:

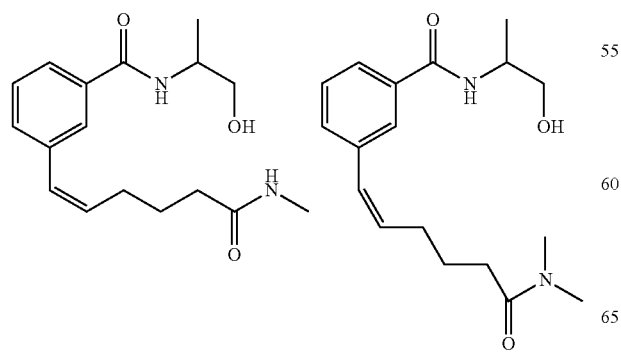

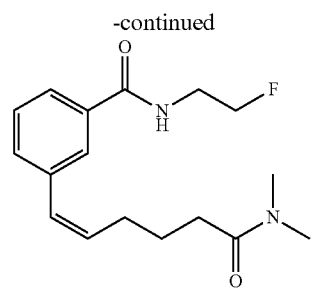

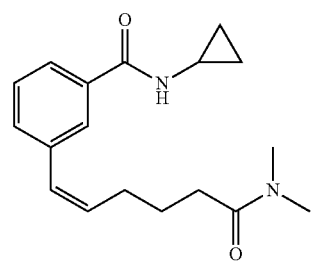

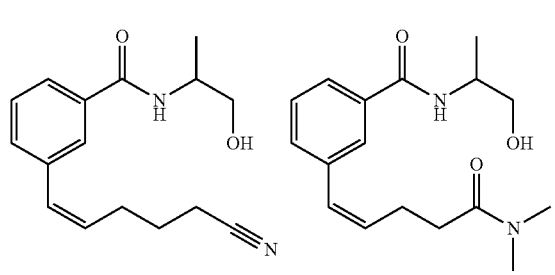

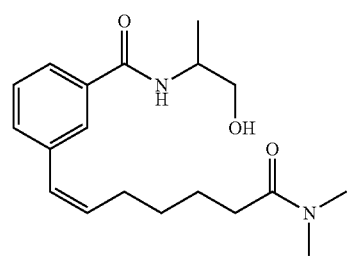

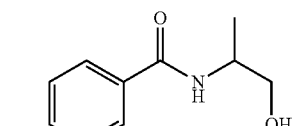

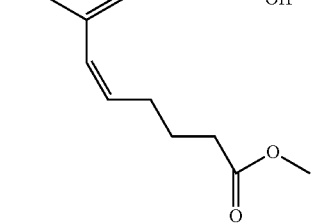

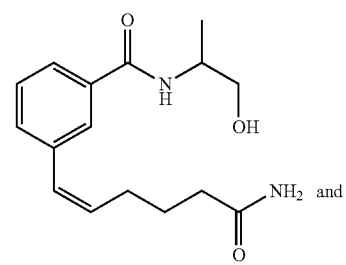

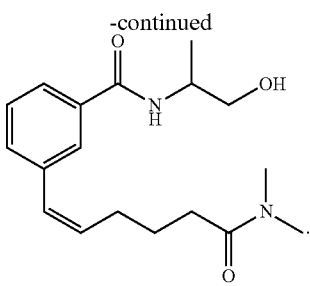

9. A process according to claim 1, wherein said compound of formula V is of formula Va

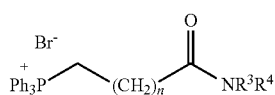

wherein $R^3$ and $R^4$ are both alkyl.

10. A process according to claim 9 wherein $R^3$ and $R^4$ are both methyl.

11. A process according to claim 9, which further comprises the step of preparing a compound of formula Va from a compound of formula Vb.

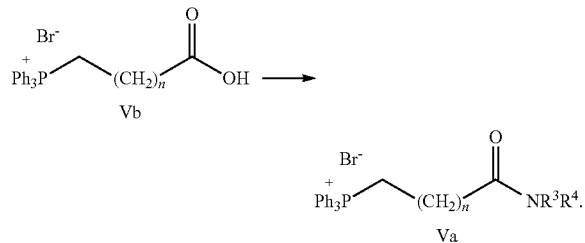

12. A process according to claim 11 which comprises treating said compound of formula Vb with (a) ethyl chloroformate and triethylamine to form a mixed anhydride; and (b) reacting said mixed anhydride with an amine salt $NHR^3R^4.HCl$.

13. A process according to claim 12 wherein step (a) is carried out in THF or anhydrous dichloromethane.

14. A process according to claim 12, wherein the amine salt $NHR^3R^4.HCl$ used in step (b) is recrystallised from methanol/diethyl ether prior to use.

15. A process according to claim 9, wherein said compound of formula Va is purified by trituration with diethyl ether.

16. A process according to claim 1, wherein said compound of formula V is dissolved in anhydrous dichloromethane.

17. A process according to claim 1, wherein step (i) comprises treating the compound of formula V with potassium hexamethyldisilazide in THF or toluene prior to addition of the compound of formula IV.

18. A process according to claim 17 wherein the potassium hexamethyldisilazide is added at a temperature of less than about 5° C.

19. A process according to claim 1, wherein said compound of formula V is of formula Vb

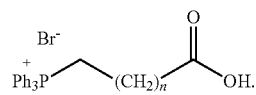

20. A process according to claim 19 wherein step (i) comprises adding sodium hydride in a mixture of anhydrous dichloromethane and anhydrous THF to a mixture of said compound of formula Vb in anhydrous dichloromethane.

21. A process according to claim 1, wherein said compound of formula IV is dissolved in THF.

22. A process according to claim 1, wherein the compound of formula IV is added to the reaction mixture at a temperature of less than about 5° C.

23. A process according to claim 1, wherein step (i) comprises hydrolysing the crude product of the reaction of said compound of formula IV and said compound of formula V.

24. A process according to claim 1, which comprises the step of isolating isomer IIIb from a mixture of isomers IIIa and IIIb prior to step (ii).

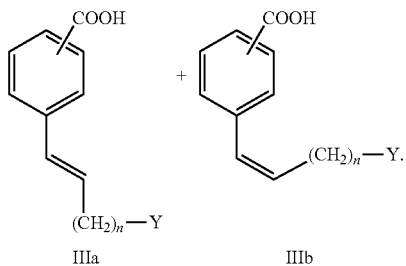

25. A process according to claim 24 which comprises the steps of:
 (a) forming a salt of isomers IIIa and IIIb;
 (b) separating the salt of isomer IIIb from the salt of isomer IIIa; and
 (c) treating the salt of isomer IIIb obtained in step (b) to form isomer IIIb.

26. A process according to claim 25 wherein step (a) comprises treating the mixture of isomers IIIa and IIIb with 4-dimethylaminopyridine (DMAP) to form the corresponding DMAP salts.

27. A process according to claim 26 wherein the DMAP is dissolved in ethyl acetate.

28. A process according claim 25, wherein step (b) comprises separating the salt form of isomer IIIb by crystallisation.

29. A process according to claim 28 wherein step (b) comprises crystallising the salt form of isomer IIIb from a solvent mixture of diethyl ether and ethyl acetate.

30. A process according claim 25, wherein step (c) comprises treating the salt form of isomer IIIb with an acid to form isomer IIIb.

31. A process according to claim 30 wherein the acid is HCl.

32. A process according to claim 1, wherein step (ii) comprises reacting said compound of formula IIIb with a compound of formula II in the presence of a coupling agent.

33. A process according to claim 32 wherein the coupling agent is 1,1'-carbonyldiimidazole (CDI).

34. A process according to claim 33 wherein step (ii) comprises dissolving said compound of formula IIIb and CDI in anhydrous DMF and adding thereto said compound of formula II in anhydrous DMF.

35. A process according to claim 32 wherein the coupling agent is 1-(3-dimethylaminopropyl)-ethylcarbodiimide hydrochloride (EDCI).

36. A process according to claim 35 wherein step (ii) comprises dissolving said compound of formula IIIb and ECDI in anhydrous dichloromethane and adding thereto N-ethyl diisopropylamine and said compound of formula II.

37. A process according to claim 1, wherein step (ii) comprises treating said compound of formula IIIb with a compound of formula II.b to form a compound of formula Ib

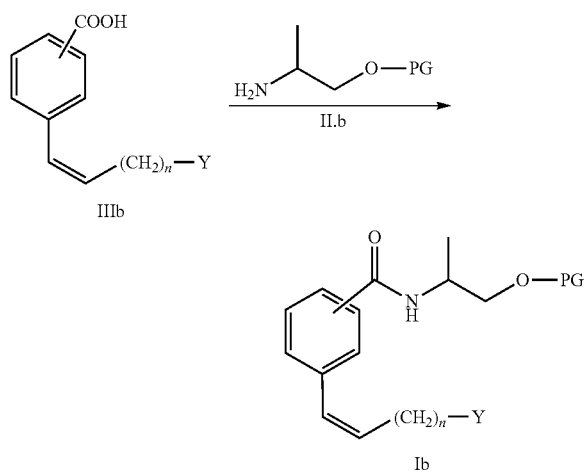

wherein PG is a hydroxyl protecting group.

38. A process according to claim 37 wherein the hydroxyl protecting group is a silyl protecting group.

39. A process according to claim 37 wherein the hydroxyl protecting group is selected from triisopropyl and trimethylsilyl.

40. A process according to claim 39 which comprises treating 2-amino-1-propanol with chorotrimethylsilane and imidazole in dichloromethane to form a trimethylsilyl-protected compound of formula IIb.

41. A process according to claim 40 wherein the trimethylsilyl-protected compound of formula IIb is used directly in step (ii) in solution form without further purification.

42. A process according to claim 39 which comprises treating 2-amino-1-propanol in anhydrous dichloromethane with 2,6-lutidine and triisopropylsilyl trifluromethane sulfonate to form a triisopropylsilyl-protected compound of formula IIb.

43. A process according to claim 42 wherein the triisopropylsilyl-protected compound of formula IIb is used directly in step (ii) without further purification.

44. A process according to claim 37, wherein said compound of formula IIb is of the formula

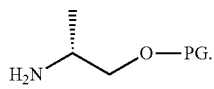

45. A process according to claim 37, which further comprises the step of removing the protecting group PG from said compound of formula Ib to form a compound of formula Ia

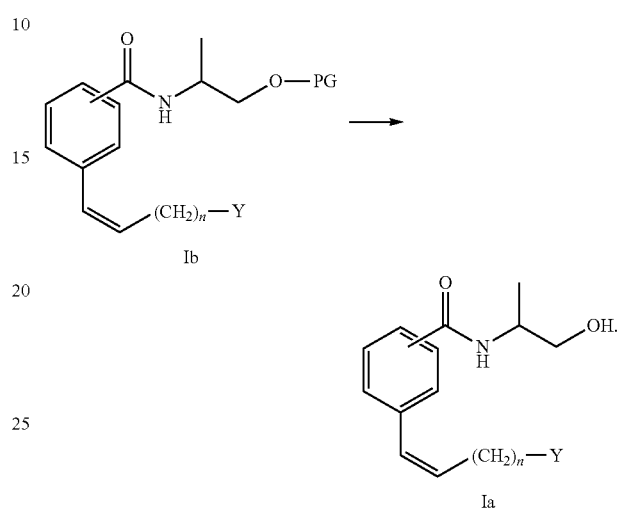

46. A process according to claim 45 which comprises treating said compound of formula Ib with TBAF in THF.

47. A process for preparing VSN-16

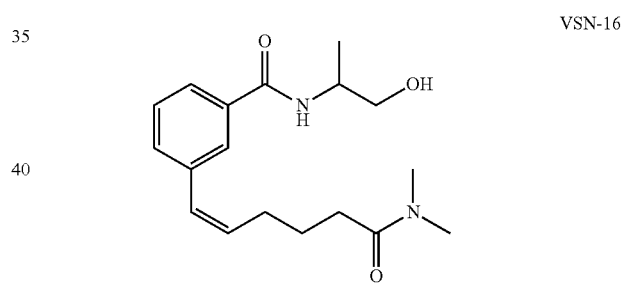

said process comprising the steps of:
treating a compound of formula IV.1 with a compound of formula V.1 to form a compound of formula IIIb.1;
treating said compound of formula IIIb.1 with a compound of formula IIb.1, where PG is a protecting group, to form a compound of formula Ib.1; and
removing protecting group PG from said compound of formula Ib.1 to form VSN-16

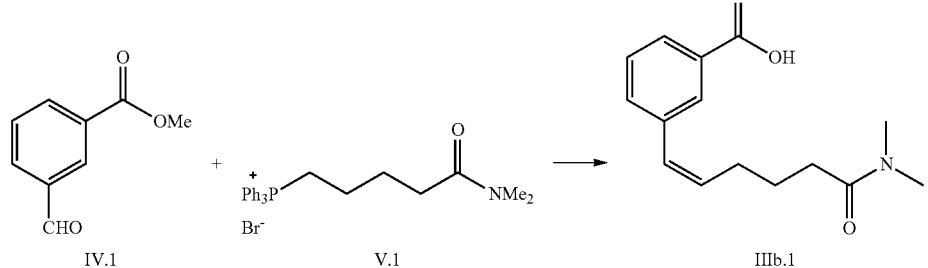

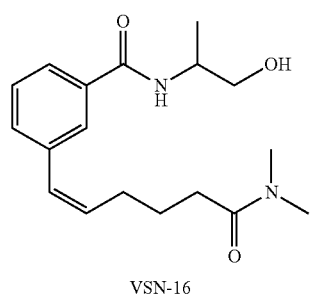
VSN-16
-continued
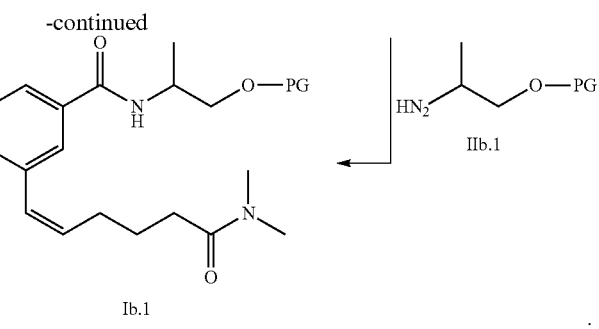
Ib.1   IIb.1
* * * * *